(12) United States Patent
Akunne et al.

(10) Patent No.: US 6,566,400 B1
(45) Date of Patent: May 20, 2003

(54) METHODS FOR TREATING PHYSIOLOGICAL CONDITIONS ASSOCIATED WITH THE USE, OR SEQUELAE OF USE, OF COCAINE OR OTHER PSYCHOMOTOR STIMULANTS

(75) Inventors: Hyacinth Chi Akunne, Ann Arbor, MI (US); Ann Elizabeth Corbin, Ann Arbor, MI (US); David James Dooley, South Lyon, MI (US); Alysia Latrese Green, Detroit, MI (US); Thomas Gary Heffner, Ann Arbor, MI (US)

(73) Assignee: Pfizer Inc., Ann Arbor, MI (US)

( * ) Notice: Subject to any disclaimer, the term of this patent is extended or adjusted under 35 U.S.C. 154(b) by 0 days.

(21) Appl. No.: 09/650,313

(22) Filed: Aug. 29, 2000

Related U.S. Application Data

(62) Division of application No. 09/485,022, filed as application No. PCT/US98/16847 on Aug. 13, 1998, now Pat. No. 6,194,459.
(60) Provisional application No. 60/056,189, filed on Aug. 19, 1997.

(51) Int. Cl.$^7$ .................... A61K 31/195; A61K 31/215
(52) U.S. Cl. .................... 514/561; 514/529; 514/530
(58) Field of Search .................... 514/561, 529, 514/530

(56) References Cited

PUBLICATIONS

Nicolodi et al., International Journal of Clinical Pharmacology Research, 17 (2–3), 97–100, 1997.*
Bailey et al., Br. J. Pharmacol. (17, Proc. Supp, 29P) (1996).*

* cited by examiner

*Primary Examiner*—Phyllis G. Spivack
(74) *Attorney, Agent, or Firm*—David R. Kurlandsky; Karen DeBenedictis

(57) ABSTRACT

Cyclic amino acids, such as gabapentin and pregabalin, are used for treating physiological conditions associated with the use, or sequelae of use, of cocaine or other psychomotor stimulants and other addictive drugs/substances. Physiological conditions include stimulant-induced toxicities.

12 Claims, 4 Drawing Sheets

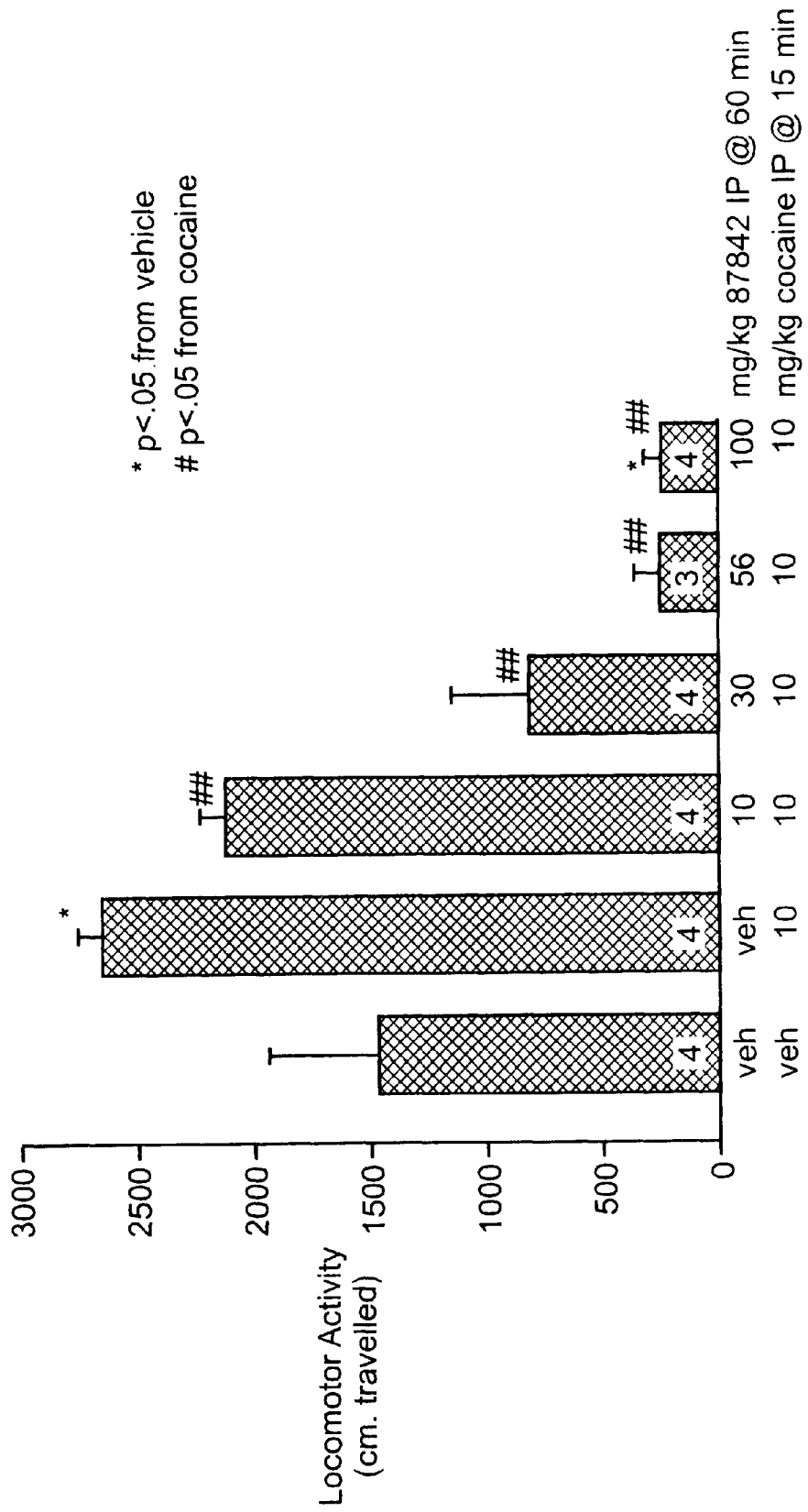
FIG-1 Effect of PD 87842 (Gabapentin) on cocaine stimulated locomotion in rats dosed IP (n=3-4)

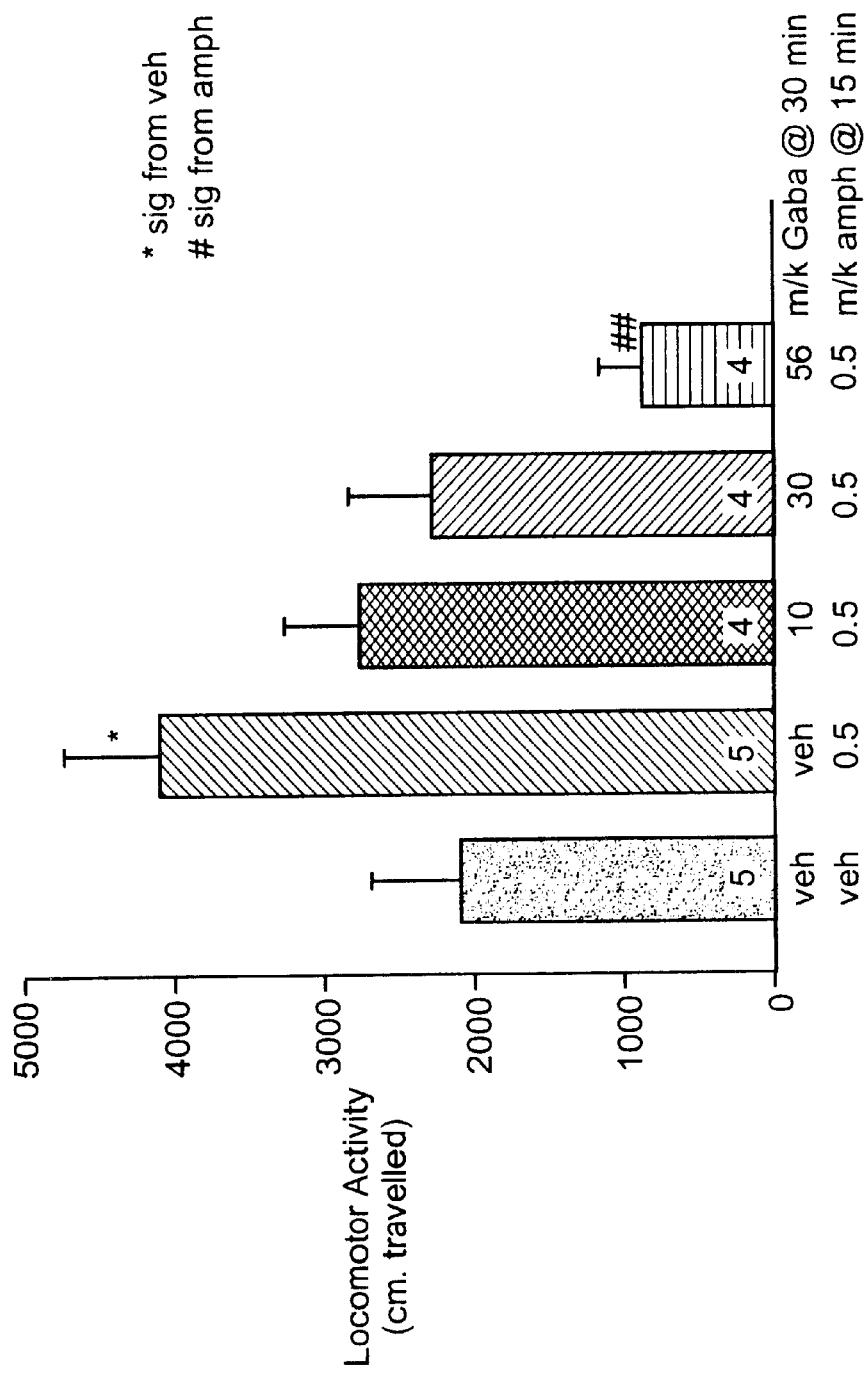
FIG-2 Effect of Gabapentin on amphetamine stimulated locomotion in rats dosed IP (n=4-5)

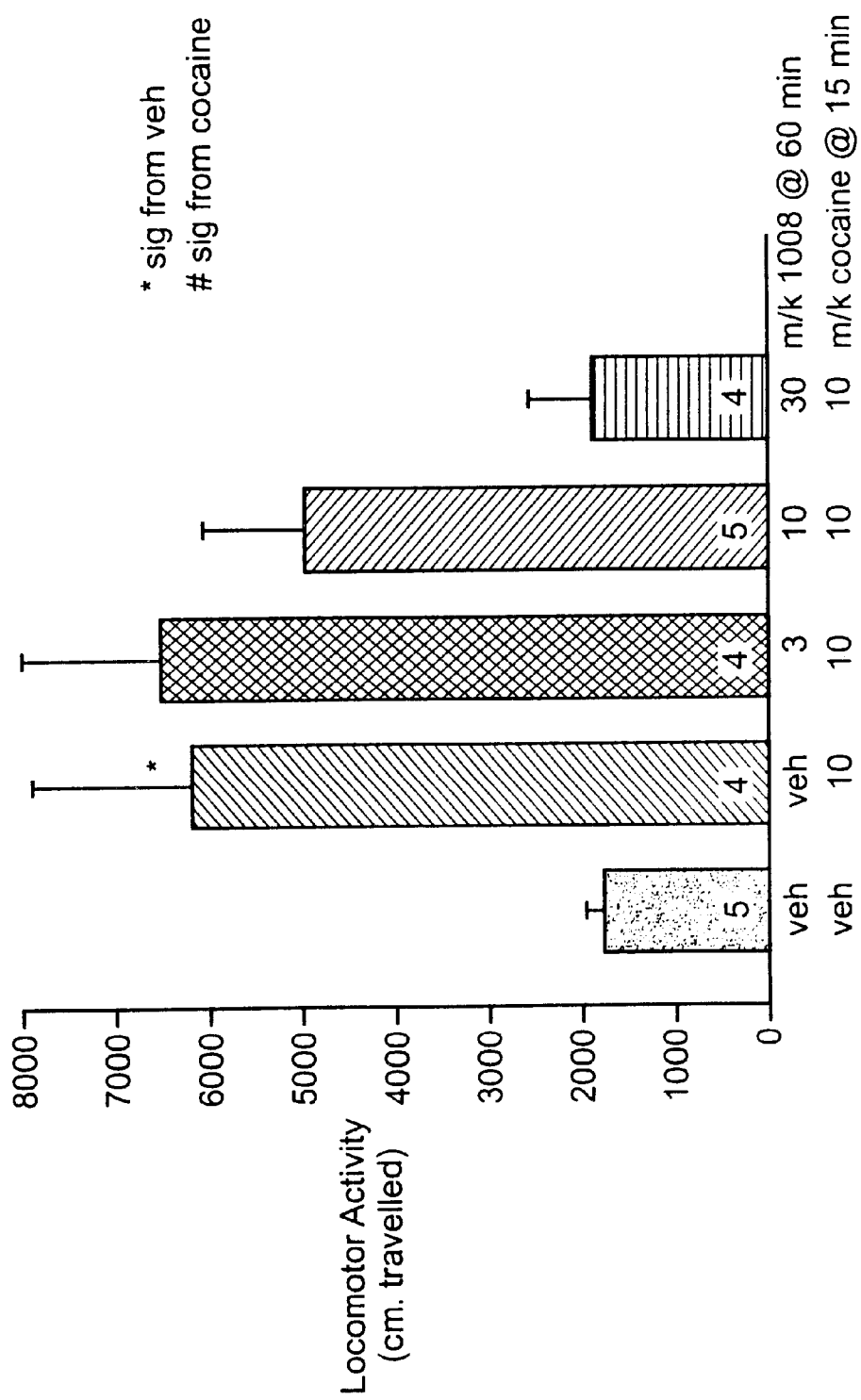
FIG-3 Effect of CI-1008 on cocaine stimulated locomotion in rats dosed IP (n=4-5)

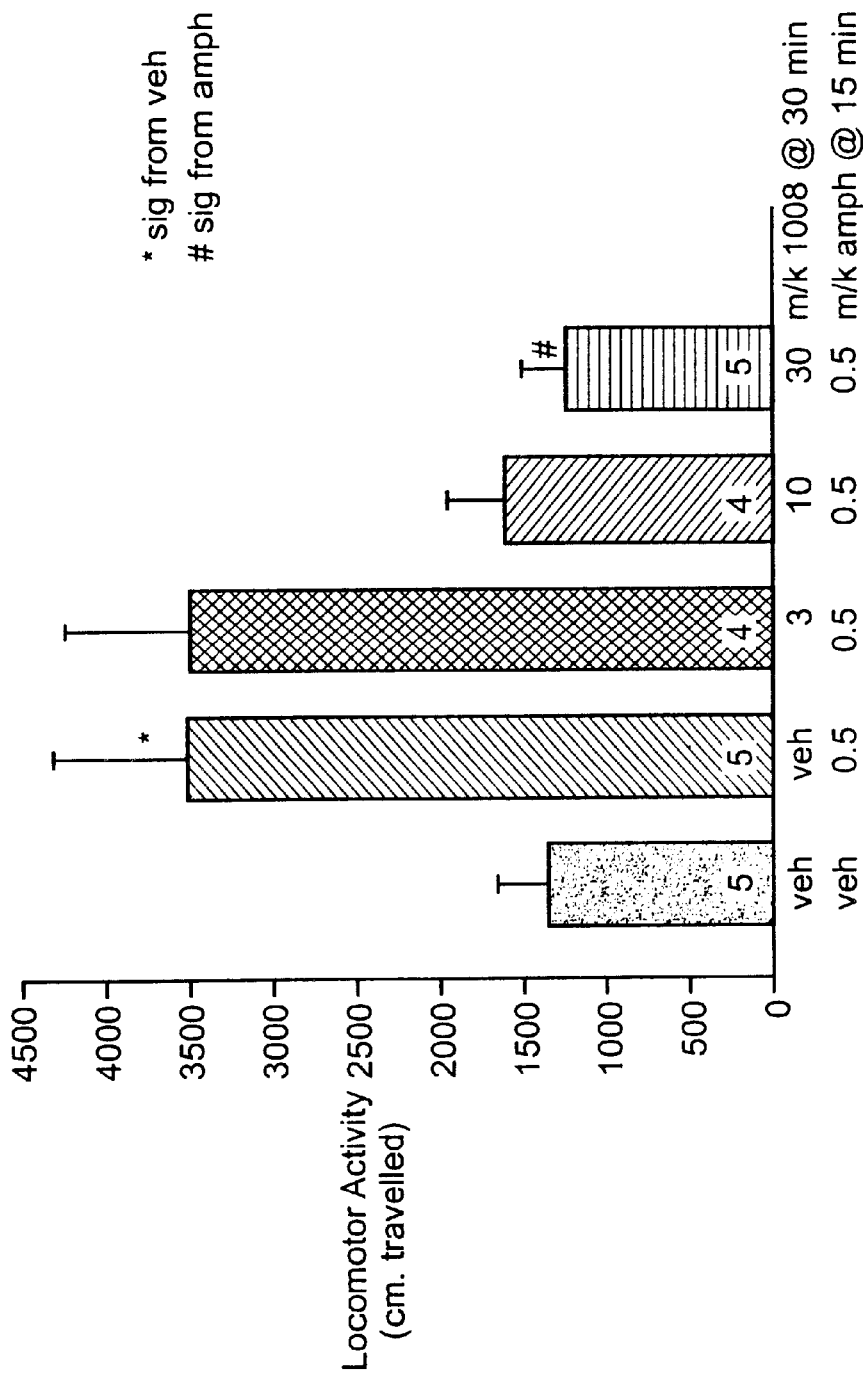
FIG-4 Effect of CI-1008 on amphetamine stimulated locomotion in rats dosed IP (n=4-5)

METHODS FOR TREATING PHYSIOLOGICAL CONDITIONS ASSOCIATED WITH THE USE, OR SEQUELAE OF USE, OF COCAINE OR OTHER PSYCHOMOTOR STIMULANTS

This is a division of U.S. Ser. No. 09/485,022 filed Feb. 2, 2000. U.S. Pat. No. 6,194,459, which is a 371 of PCT/US98/16847 filed Aug. 13, 1998 which claims benefit of No. 60/056,189 filed Aug. 19, 1997.

FIELD OF THE INVENTION

The present invention relates to novel therapeutic uses of a known compound, gabapentin, its derivatives, and pharmaceutically acceptable salts. The present invention concerns a method for treating physiological conditions associated with the use, or sequelae of use, of cocaine or other addictive drugs/substances in a mammal in need of such treatment.

BACKGROUND OF THE INVENTION

Cocaine abuse and addiction have increased greatly during the last decade. Cocaine is a member of the class of drugs known as psychomotor stimulants. The term "psychomotor stimulants" refers to a class of drugs that stimulates a mammal's central nervous system. Examples of psychomotor stimulants include, but are not limited to amphetamine, methamphetamine, methylphenidate, and other agents with similar pharmacological actions.

Often the use, or sequelae of use, of cocaine or other psychomotor stimulants is associated with psychopathological conditions. The psychopathological conditions of cocaine and other psychomotor stimulants are generally similar, or in some cases identical. Craving, dysphoria, and depression are important components of withdrawal syndromes from cocaine and psychomotor stimulants other than cocaine.

In animals, repeated exposure to cocaine can induce supersensitivity to many of its effects including seizures, behavioral hyperactivity, and stereotypy. The development of supersensitivity to the convulsant effects of cocaine following repeated exposures is similar in some respects to the phenomenon known as kindling, the reduction of seizure threshold after repeated electrical stimulation of certain brain regions. The brain regions in which kindling is obtained include portions of the limbic system, areas of the brain believed to be involved in normal emotional behaviors, as well as some psychopathological behaviors (eg, Post et al, 1972). Thus, it has been suggested that a kindling-like phenomenon may be involved in the development of cocaine addiction and craving.

U.S. Pat. No. 4,024,175, its divisional U.S. Pat. No. 4,087,544, and U.S. Pat. No. 5,563,175 cover the compounds of the instant invention, methods for preparing them, and several uses thereof. The uses disclosed are: protective effect against cramp induced by thiosemicarbazide; protective action against cardiazole cramp; the cerebral diseases epilepsy, faintness attacks, hypokinesia, and cranial traumas; and improvement in cerebral functions. The compounds are useful in geriatric patients.

U.S. Pat. Nos. 5,025,035 and 5,084,479 also disclose methods for using the compounds of the instant invention. U.S. Pat. No. 5,025,035 discloses methods of treating depression. U.S. Pat. No. 5,084,479 discloses methods for treating neurodegenerative diseases. The patents are hereby incorporated by reference.

There is no disclosure in the above references to suggest the present invention's uses of compounds of U.S. Pat. No. 4,024,175, its divisional U.S. Pat. No. 4,087,544, and U.S. Pat. No. 5,563,175 to treat physiological conditions associated with the use, or sequelae of use, of cocaine or other addictive agents.

SUMMARY OF THE INVENTION

To the extent that kindling-like phenomena are involved, it has been discovered that gabapentin, its derivatives and pharmaceutically acceptable salts, will be effective in treating not only seizures, but also physiological abnormalities or toxicities caused by repeated exposure to cocaine and/or other psychomotor stimulants.

It has also been discovered that gabapentin, its derivatives, and pharmaceutically acceptable salts will be effective in treating physiological conditions caused by repeated exposure to addictive drugs/substances other than cocaine.

There have been various reports that provide functional and neurochemical evidence that there are specific neurobiological commonalties between addictive drugs/substances. Dopamine neurotransmission in the mesolimbic system, and particularly in the nucleus accumbens, is currently recognized as a critical target of drugs of abuse (Wise R. A. and Bozarth M. A., *Psychol Rev.*,1987;94:469–492; Koob G. F., *Trends Pharmacol. Sci.*, 1992; 13:177–184; Di Chiara G., *Drug Alcohol Depend.*, 1995;38:95–121). Among drugs active in the central nervous system, the ability to act as a rewarding stimulus, to activate motor behavior, and to increase synaptic dopamine concentrations in the mesolimbic system are in some way linked. Drugs that are abused are from diverse classes (depressants, stimulants, nicotine, opiates, heroin, barbiturates, hallucinogens, sedative/hypnotics, solvents, steroids) suggesting that they might act through a common mediator. It has been determined that drugs abused by humans stimulate dopamine transmission in the nucleus accumbens while drugs with aversive properties reduced dopamine release and drugs not abused by humans failed to modify synaptic dopamine concentrations (Di Chiara G. and Imperato A., *Proc. Natl. Acad. Sci.*, 1988;85:5274–5278). It has been discovered that successful treatment of a psychostimulant-induced physiological condition with gabapentin, its derivatives, and pharmaceutically acceptable salts can be extended to treating the physiological conditions of drugs of abuse other than cocaine and other psychomotor stimulants.

In one embodiment, the present invention discloses a method for treating physiological conditions associated with the use, or sequelae of use, of psychomotor stimulants such as cocaine and other abused drugs/substances. The present invention comprises administering a therapeutically effective amount of a compound of Formula I:

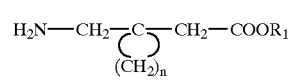

wherein $R_1$ is hydrogen or a lower alkyl and n is 4, 5, or 6 or a pharmaceutically acceptable salt thereof, in unit dosage form, to a mammal in need of said treatment. Preferably, it has been found that the administration of gabapentin is effective in treating physiological conditions associated with the use, or sequelae of use, of psychomotor stimulants and other addictive drugs/substances.

In another preferred embodiment, the present invention comprises administering a therapeutically effective amount of a compound of Formula II:

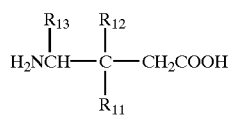

wherein $R_{11}$ is a straight or branched alkyl of from 1 to 6 carbon atoms, phenyl, or cycloalkyl having from 3 to 6 carbon atoms; $R_{12}$ is hydrogen or methyl; and $R_{13}$ is hydrogen, methyl, or carboxyl; or an individual enantiomeric isomer thereof; or a pharmaceutically acceptable salt thereof, in unit dosage form, to a mammal in need of said treatment. Preferably, it has been found that the administration of pregabalin((S)-3-(aminoethyl)-5-methylhexanoic acid) is effective in treating physiological conditions associated with the use, or sequelae of use, of psychomotor stimulants and other addictive drugs/substances.

The term "physiological conditions" associated with the use, or sequelae of use, of psychomotor stimulants or other addictive drugs/substances is meant to cover a broad number of pathological states. Nonlimiting examples of pathological states include tachycardia, hypertension, mydriasis and agitation, death may be caused by a cardiovascular collapse or respiratory failure, viral hepatitis intracranial hemorrhages, cardiac arrhythmias secondary to hypertension, necrotizing angitits, fever, leukemoid reaction, disseminated intravascular coagulation, rhabdomyolysis, and acute renal failure. A number of other pathophysiological conditions that can be treated by the methods of the present invention are referenced in "The Pathology of Drug Abuse", Steven B. Karch, 1993, CRC Press, Inc.

The term "addictive drugs/substances" is meant to cover drugs/substances other than psychomotor stimulants that are abused, and preferably those drugs/substances that target dopamine neurotransmission. Addictive drugs/substances include but are not limited to depressants, nicotine, opiates, heroin, barbiturates, hallucinogens, sedative/hypnotics, solvents, steroids. Specific non-limiting examples of addictive drugs/substances include alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, morphine, neperidine, phenomorphan, phenoperidine, piritradide, pholcodine, proheptazoine, properidine, propiran, racemoramide, thebacon, trimeperidine, and the pharmaceutically acceptable salts thereof.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which:

FIG. 1 demonstrates how gabapentin dose dependently blocked cocaine-stimulated increase in locomotor activity in rats.

FIG. 2 demonstrates how gabapentin dose dependently blocked amphetamine-stimulated increase in locomotor activity in rats.

FIG. 3 demonstrates how pregabalin dose dependently blocked cocaine-stimulated increase in locomotor activity in rats.

FIG. 4 demonstrates pregabalin dose dependently blocked amphetamine-stimulated increase in locomotor activity in rats.

DETAILED DESCRIPTION OF THE INVENTION

The present invention relates to novel methods of treating physiological conditions associated with the use, or sequelae of use, of cocaine or other psychomotor stimulants and other addictive drugs/substances in a mammal in need of such treatment. The treatment comprises administering in unit dosage form an effective amount of a compound of Formula I:

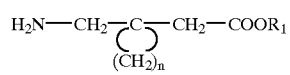

wherein $R_1$ is hydrogen or a lower alkyl and n is 4, 5, or 6 or a pharmaceutically acceptable salt thereof, in unit dosage form, to a mammal in need of said treatment. The term lower alkyl includes straight or branched chain alkyl groups of up to 8 carbon atoms.

Preferred compounds of Formula I above include but are not limited to 1-aminomethyl-1-cyclohexane-acetic acid, ethyl 1-aminomethyl-1-cyclohexane-acetate, 1-aminomethyl-1-cycloheptane-acetic acid, 1-aminomethyl-1-cyclopentane-acetic acid, methyl 1-aminomethyl-1-cyclohexane-acetate, n-butyl 1-aminomethyl-1-cyclohexane-acetate, methyl 1-aminomethyl-1-cycloheptane-acetate, n-butyl 1-aminomethyl-1-cycloheptane-acetate, toluene sulfonate, 1-aminomethyl-1-cyclopentane-acetate, benzene-sulfonate, and n-butyl 1-aminomethyl-1-cyclopentane-acetate.

The most preferred compound is 1-aminomethyl-cyclohexane acetic acid (gabapentin).

In another preferred embodiment, the present invention comprises administering a therapeutically effective amount of a compound of Formula II:

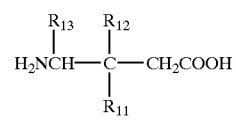

wherein $R_{11}$ is a straight or branched alkyl of from 1 to 6 carbon atoms, phenyl, or cycloalkyl having from 3 to 6 carbon atoms; $R_{12}$ is hydrogen or methyl; and $R_{13}$ is hydrogen, methyl, or carboxyl; or an individual enantiomeric isomer thereof; or a pharmaceutically acceptable salt thereof, in unit dosage form, to a mammal in need of said treatment. The preferred compound of Formula II is pregabalin.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil; sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits, but for practical purposes it is preferably present in a concentration of at least 10% in a solid composition and at last 2% in a primary liquid composition. The most satisfactory compositions are those in which a much higher proportion of the active ingredient is present.

The method of administration of the pharmacotherapies may vary. For the most part, however, routes of administration of the subject compound or its salts are oral or parenteral. For example, a useful intravenous dose is between 5 and 50 mg and a useful oral dosage is between 20 and 200 mg. The exact individual dosage, as well as the daily dosage, will be determined according to standard principles under the direction of a physician.

As noted, gabapentin is recognized as a particularly effective pharmacotherapy for use in the subject method, gabapentin will typically be administered as an injectable, capsule, or tablet. Preparation of these gabapentin containing dosage forms are as follows:

Injectables, 1 mg to 100 mg/mL
  Gabapentin
  Water for Injection USP q.s.
  The compound or a suitable salt thereof is dissolved in water and passed through a 0.2-micron filter. Aliquots of the filtered solution are added to ampoules or vials, sealed, and sterilized.

Capsules, 50, 100, 200, 300, or 400 mg
  Gabapentin, 250 g
  Lactose USP, Anhydrous q.s. or 250 g
  Sterotex Powder HM, 5 g
  Combine the compound and the lactose in a tumble blend for 2 minutes, blend for 1 minute with the intensifier bar, and then tumble blend again for 1 minute. A portion of the bend is then mixed with the Sterotex powder, passed through a No. 30 screen, and added back to the remainder of the blend. The mixed ingredients are then blended for 1 minute, blended with the intensifier bar for 30 seconds, and tumble blended for an additional minute. The appropriately sized capsules are filled with 141, 352.5, or 705 mg of the blend, respectively, for the 50, 125, and 250 mg containing capsules.

Tablets, 5, 100, 200, 300, 400, 500, or 600 mg
  Gabapentin, 125 g
  Corn Starch NF, 200 g
  Cellulose, Microcrystalline, 46 g
  Sterotex Powder HM, 4 g
  Purified Water q.s. or 300 mL
  Combine the corn starch, the cellulose, and the compound together in a planetary mixer and mix for 2 minutes. Add the water to this combination and mix for 1 minute. The resulting mix is spread on trays and dried in a hot air oven at 500° C. until a moisture level of 1% to 2% is obtained. The dried mix is then milled with a Fitzmill through a No. RH2B screen and added back to the milled mixture, and the total blended for 5 minutes by drum rolling. Compressed tablets of 150, 375, and 750 mg, respectively, of the total mix are formed with appropriate sized punches the 50, 125, or 50 mg containing tablets.

A unit dosage form of the instant invention may also comprise other compounds useful in the therapy of neurodegenerative diseases.

The advantages of using the compounds of Formulas I and II, especially gabapentin, in the instant invention include the relatively nontoxic nature of the compound, the ease of preparation, the fact that the compound is well-tolerated, and the ease of IV administration of the drug. Further, the drug is not metabolized in the body.

The subjects as used herein are mammals, including humans.

The above disclosure generally describes the present invention. A more complete understanding can be obtained by reference to the following specific examples which are provided herein for purposes of illustration only and are not intended to be limiting unless otherwise specified.

The usefulness of compounds of Formulas I and II above, and the salts thereof as agents for treating physiological conditions associated with the use, or sequelae of use, of cocaine or other psychomotor stimulants and other addictive drugs/substances is demonstrated in standard pharmacological test procedures. Examples of standard pharmacological test procedures include, but are not limited to locomotor activity, intravenous drug self-administration in rodents or primates, conditioned place preference tests, and drug discrimination.

EXAMPLE 1

In this example, gabapentin and pregabalin were administered to rats treated with psychostimulants to determine their anti-abuse and anti-addictive potential. The effects of compounds on locomotor activity of rodents are predictive of their therapeutic anti-abuse or anti-addictive properties. The administration of cocaine (an abuse agent) or amphetamine result in increase in locomotor activity of rats, and these results were dose-dependently blocked by gabapentin and pregabalin (see FIGS. 1–4).

Description of Locomotor Activity. Test Paradigm: Locomotor Activity

Male Sprague-Dawley rats from Harlan labs (200–275 g) were used for all locomotor activity studies. Locomotor activity data (expressed as distance traveled in cm) was measured in the Omnitech Digiscan animal activity monitors. Twenty-four Omnitech chambers were used in each study, each consisting of a 16'×16' square plexiglas open field with 2 sets of 16 infrared photobeams assembled on each of the four sides of the apparatus.

1.
  Test Name: Spontaneous locomotor activity in rats
  Test Rationale: To determine the effects of compound on cocaine-stimulated locomotor activity
Cocaine Interaction Study: Rats were given saline or test drug IP 45 minutes prior to an IP saline or cocaine injection (10 mg/kg IP). Rats were then placed in separate Omnitech chambers for an additional 15-minute drug absorption period (in dark), after which time locomotor activity was measured for 1 hour (in dark). Data were expressed as distance traveled (in cm).

2.

Test Name: Spontaneous locomotor activity in rats

Test Rationale: To determine the effects of compound on amphetamine-stimulated locomotor activity Amphetamine Interaction Study: Rats were given saline or test drug and placed in Omnitech chambers for an additional 15 minutes (in dark) prior to an IP saline or d-amphetamine injection (0.5 mg/kg IP). Rats were returned to their respective chamber for a 15-minute drug absorption period, after which time locomotor activity was measured for 30 minutes (in dark). Data were expressed as distance traveled (in cm) N-4–5 rats per group.

What is claimed is:

1. A method for treating physiological conditions associated with the use, or sequelae of use, of psychomotor stimulants which comprises administering a therapeutically effective amount of a compound of Formula I:

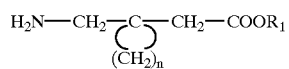

wherein $R_1$ is hydrogen or a lower alkyl and n is 4, 5, or 6 or a pharmaceutically acceptable salt thereof, in unit dosage form, to a mammal in need of said treatment.

2. A method according to claim 1, wherein the psychomotor stimulant is cocaine.

3. A method according to claim 1, wherein the psychomotor stimulant is amphetamine.

4. A method according to claim 1, wherein the physiological condition is stimulant-induced toxicities.

5. A method according to claim 1, wherein the compound is gabapentin or a pharmaceutically acceptable salt thereof.

6. A method according to claim 1, wherein an individual dose is 5 to 50 mg parenterally or 20 to 200 mg enterally of the compound or a pharmaceutically acceptable salt thereof is administered.

7. A method for treating physiological conditions associated with the use, or sequelae of use, of addictive drugs/substances which comprises administering a therapeutically effective amount of a compound of Formula I:

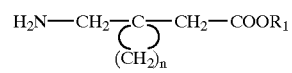

wherein $R_1$ is hydrogen or a lower alkyl and n is 4, 5, or 6 or a pharmaceutically acceptable salt thereof, in unit dosage form, to a mammal in need of said treatment, provided that when the compound is gabapentin, the addictive drug/substance is not ethanol.

8. A method according to claim 7, wherein the addictive drug/substance is nicotine.

9. A method according to claim 7, wherein the addictive drug/substance is an opiate.

10. A method according to claim 7, wherein the physiological condition is stimulant-induced toxicities.

11. A method according to claim 7, wherein the compound is gabapentin or a pharmaceutically acceptable salt thereof.

12. A method according to claim 7, wherein an individual dose is 5 to 50 mg parenterally or 20 to 200 mg enterally of the compound or a pharmaceutically acceptable salt thereof is administered.

* * * * *